United States Patent
Buford, II

(10) Patent No.: US 8,901,067 B1
(45) Date of Patent: Dec. 2, 2014

(54) FRAGRANCE COMPOSITION

(76) Inventor: Keith G. Buford, II, Sacramento, CA (US)

( * ) Notice: Subject to any disclaimer, the term of this patent is extended or adjusted under 35 U.S.C. 154(b) by 0 days.

(21) Appl. No.: 13/589,229

(22) Filed: Aug. 20, 2012

(51) Int. Cl.
*C11B 9/00* (2006.01)

(52) U.S. Cl.
USPC .............................................. 512/5

(58) Field of Classification Search
USPC .............................................. 512/5
See application file for complete search history.

(56) References Cited

U.S. PATENT DOCUMENTS

| | | | |
|---|---|---|---|
| 2,159,872 A | 5/1939 | Younghusband | |
| 2,162,584 A | 6/1939 | Kole | |
| 2,546,895 A | 3/1951 | Jarowski | |
| 2,827,164 A | 3/1958 | Anderson | |
| 4,323,176 A | 4/1982 | Sartain | |
| 4,356,938 A | 11/1982 | Kayser | |
| D270,770 S | 9/1983 | Bakic | |
| 4,793,991 A | 12/1988 | Slimak | |
| 4,848,598 A | 7/1989 | McKinney | |
| 4,886,186 A | 12/1989 | Andris | |
| 5,932,230 A * | 8/1999 | DeGrate | 424/401 |
| 6,096,010 A | 8/2000 | Walters et al. | |
| D522,696 S | 6/2006 | Severa | |
| 7,377,707 B2 | 5/2008 | Breidenbach et al. | |
| 2004/0131565 A1 | 7/2004 | Lee | |
| 2006/0275509 A1 | 12/2006 | Wegener | |
| 2008/0089916 A1 * | 4/2008 | Magee et al. | 424/401 |
| 2008/0194883 A1 | 8/2008 | Nowak et al. | |
| 2008/0219938 A1 * | 9/2008 | Grune | 424/59 |
| 2009/0095777 A1 | 4/2009 | Francavilla | |
| 2012/0093949 A1 * | 4/2012 | Steinberg | 424/727 |

OTHER PUBLICATIONS

The Vapo Family. VapoRub Topical Ointment.

* cited by examiner

*Primary Examiner* — Ling Choi
*Assistant Examiner* — Lanee Reuther
(74) *Attorney, Agent, or Firm* — Robert C Montgomery; Montgomery Patent & Design

(57) ABSTRACT

A topical salve to mask unpleasant smells is disclosed that consists of a composition having beeswax, eucalyptus oil, and menthol. The composition is placed under the nose of a user. The salve masks unpleasant strong odors, thereby allowing the user to perform the task at hand.

5 Claims, No Drawings

FRAGRANCE COMPOSITION

RELATED APPLICATIONS

Not Applicable.

FIELD OF THE INVENTION

The presently disclosed subject matter is directed to topical salves for masking unpleasant odors. More particularly the present invention is directed to a topical salve containing beeswax, eucalyptus oil, and menthol.

BACKGROUND OF THE INVENTION

Emergency medical technicians, doctor, nurses, morgue attendants, funeral workers, animal handlers and numerous other groups of people often must deal with awful smells. Decaying flesh, rotten meat and fish, vomit, and defecation are all overwhelming odors that must be dealt with in some occupational areas.

One (1) useful trick is to dab a strong smelling salve such as VICKS VAPORUB® under their nose and, if required, wear a mask. The strong smell of the compound hides unpleasant smells such as vomit, defecation, and even death. With such a compound in place many people can perform their jobs without choking, gagging, or vomiting themselves.

While strong smelling salves are useful, they are not necessarily the best solution. One (1) problem is that while such salves hide unpleasant smells, they themselves are not all that pleasant. Accordingly, there exists a need for a more pleasant smelling salve to hide bad odors. Beneficially such a salve would be easy to use, low in cost, and safe for use.

SUMMARY OF THE INVENTION

The principles of the present invention provide for a relatively pleasant smelling salve that hides unpleasant odors and that is easy to use, low in cost, and safe.

A salve in accord with the present invention is a fragrance ointment that hides unpleasant strong odors and eliminates the gag reflex allowing the user to perform the tasks at hand.

A topical salve composition that is in accord with the present invention is formulated for application under the nose to reduce the scent of obnoxious odors. That composition includes an effective amount of beeswax, coconut oil, and eucalyptus oil. The beeswax composition may be approximately forty-eight percent (48%) beeswax and the coconut oil may be forty-eight percent (48%). The topical salve may further include avocado oil and possibly menthol and spearmint oil. In practice the topical salve may be thirty-three-point-sixteen percent (33.16%) beeswax, thirty-three-point-sixteen percent (33.16%) coconut oil, sixteen-point-fifty-eight percent (16.58%) avocado oil, eight-point-twenty-eight percent (8.28%) menthol, four-point-forty-one percent (4.41%) spearmint oil, and four-point-forty-one percent (4.41%) eucalyptus oil.

The present invention also includes a topical salve for reducing the gag reflex in man comprising beeswax, coconut oil, and avocado oil. That salve may also include menthol. In one (1) embodiment that salve is about twenty-five percent (25%) beeswax, twenty-five percent (25%) coconut oil, twenty-five percent (25%) avocado oil, and twenty-five percent (25%) menthol. That salve may also include spearmint oil. In one (1) such composition the topical salve will be about twenty-seven percent (27%) beeswax, twenty-five percent (27%) coconut oil, thirteen-point-five percent (13.5%) avocado oil, thirteen-point-five percent (13.5%) menthol, and nineteen-point-two percent (19.2%) spearmint oil.

The present invention further provides for the use of beeswax and coconut oil in a preparation to reduce the impact of foul odors on man. Such a preparation may also include eucalyptus oil. In one (1) such preparation the embodiment is forty-six-point-eighty-eight percent (46.88%) beeswax, forty-six-point-eighty-eight percent (46.88%) coconut oil, and six-point-twenty-four percent (6.24%) eucalyptus oil. The inventive use of beeswax and coconut oil may also include avocado oil and menthol, beneficially in equal parts. The inventive use of beeswax and coconut oil may include the spearmint oil, possibly with the addition of eucalyptus oil.

DETAILED DESCRIPTION OF THE PREFERRED EMBODIMENT

The present invention is a fragrance ointment in the form of a salve. As used herein:

"essential oils" refers to any concentrated volatile aromatic compound extracted from plants with the general propensity of being hydrophilic;

"fragrance" refers to any substance such as perfume designed to emit an aromatic and pleasant scent;

"lubricant" refers to any composition or a property thereof that is hygroscopic, prevents dryness, and otherwise moisturizes an application area;

"odoriferous compound" refers to a mixture of fragrances or essential oils to emit a pleasant scent; and, "ointment" refers generally to a salve having active ingredients which are applied to the skin.

The present invention is a fragrance ointment suitable for topical application to areas of a user's skin beneath the nose and which masks highly objectionable surrounding odors from being sensed by the user. The fragrance ointment is usable for calming the user's gag reflex. The fragrance ointment is particularly useful for persons in occupations such as, but not limited to: firefighters, police officers, medical personnel, or the like who are exposed to aromas from decaying animals or bodies, vomit, or defecation.

Typically, the preferred fragrance ointment is a formulaic mixture of an ointment, at least one fragrance, at least one essential oil, and a lubricant. More specifically, the preferred fragrance ointment comprises a formulaic blend of bees wax; coconut oil; and eucalyptus oil that produces an aromatic scent. The ingredients of the preferred fragrance ointment are prepared in the manner described below.

An example of the preferred fragrance ointment of the present invention is prepared by combining follows:

| Component | Amount (Vol %) |
| --- | --- |
| Bees Wax | 46.88 |
| Coconut Oil | 46.88 |
| Eucalyptus Oil | 6.24 |

An alternate composition of the present invention comprises a formulaic blend of bees wax ointment; coconut oil and avocado oils; and menthol as a fragrance for an aromatic scent. Those ingredients are prepared in the manner described below and applied where desired.

An example of a preferred essential composition of the present invention is prepared a follows:

| Component | Amount (Vol %) |
|---|---|
| Bees Wax | 25.00 |
| Coconut Oil | 25.00 |
| Avocado Oil | 25.00 |
| Menthol | 25.00 |

Another composition of the present invention comprises a formulaic blend of bees wax; coconut oil and avocado oils; and menthol and spearmint oil. The ingredients of that composition are prepared in the manner described below and applied where desired.

An example of a preferred essential composition of the present invention is prepared a follows:

| Component | Amount (Vol %) |
|---|---|
| Bees Wax | 27.03 |
| Coconut Oil | 27.03 |
| Avocado Oil | 13.51 |
| Menthol | 13.24 |
| Spearmint Oil | 19.19 |

Yet another alternate essential composition of the present invention may be utilized and comprises a formulaic blend of bees wax; coconut oil and avocado oils; and menthol, eucalyptus oil, and spearmint oil. The ingredients of that composition are prepared in the manner described below and applied to the surface of the skin where desired.

An example of a preferred essential composition of the present invention is prepared a follows:

| Component | Amount (Vol %) |
|---|---|
| Bees Wax | 33.16 |
| Coconut Oil | 33.16 |
| Avocado Oil | 16.58 |
| Menthol | 8.28 |
| Spearmint Oil | 4.41 |
| Eucalyptus Oil | 4.41 |

It is envisioned that other styles and configurations of the present invention can be easily incorporated into the teachings of the present invention, and various configurations are shown and described for purposes of clarity and disclosure and not by way of limitation of scope of the invention.

In each configuration, the physical appearance of the composition comprises a waxy, solid substance having a yellowish color which can be easily handled by a user during application.

The preferred embodiment of the present invention can be utilized by the common user in a simple and effortless manner with little or no training. The preparation and processing of individual ingredients may be achieved by performing the following steps:

Essential Composition Preparation—Placing bees wax in a mixing vessel; adding components in order of percentage while mixing; continuing to mix until blended; and, placing the essential composition into bottles for storage or packaging.

The essential composition is envisioned to be purchased in locations where consumer care products are typically sold. The essential composition is preferably packaged in a cylindrical lipstick-style tube. After initial purchase of the essential composition, preparation is envisioned to take place as follows: utilizing a desired amount of the essential composition within the prepackaged tube, applying a desired amount of the composition beneath the nose and above an upper lip of a user; reapplying as needed; and enjoying the odor masking benefits of the essential composition.

The foregoing descriptions of specific embodiments of the present invention have been presented for purposes of illustration and description. They are not intended to be exhaustive or to limit the invention and method of use to the precise forms disclosed. Obviously many modifications and variations are possible in light of the above teaching. The embodiment was chosen and described in order to best explain the principles of the invention and its practical application, and to thereby enable others skilled in the art to best utilize the invention and various embodiments with various modifications as are suited to the particular use contemplated. It is understood that various omissions or substitutions of equivalents are contemplated as circumstance may suggest or render expedient, but is intended to cover the application or implementation without departing from the spirit or scope of the claims of the present invention.

What is claimed is:

1. A topical salve composition formulated for application under the nose to reduce the scent of obnoxious odors, comprising an active agent that includes 33.16 vol. % of beeswax, 33.16 vol. % of coconut oil, 16.58 vol. % of avocado oil, 8.28 vol. % of menthol, 4.41 vol. % of spearmint oil, and 4.41 vol. % of eucalyptus oil.

2. A method of providing a topical salve for reducing the gag reflex in man, comprising mixing beeswax, coconut oil, and avocado oil, and then 25 vol. % menthol to form the salve; and, applying a desired amount of the salve adjacent to a nose in order to mask a malodor; wherein the vol. % is based on a total volume of the salve.

3. The method of claim 2, wherein the beeswax is 25 vol. %, coconut oil is 25 vol. %, and avocado oil is 25 vol. %.

4. The method of claim 2, further comprising the step of adding spearmint oil to the salve.

5. A method of providing a topical salve for reducing the gag reflex in man, comprising the steps of: providing said salve including 27.03 vol. % of beeswax, 27.03 vol. % of coconut oil, 13.51 vol. % of avocado oil, 13.24 vol. % of menthol, and 19.19 vol. % of spearmint oil; and, applying a desired amount of said salve adjacent to a nose in order to mask a malodor.

* * * * *